United States Patent
Yang et al.

(10) Patent No.: US 11,478,654 B2
(45) Date of Patent: Oct. 25, 2022

(54) PACKAGING STRUCTURE AND PACKAGING METHOD FOR RETINAL PROSTHESIS IMPLANTED CHIP

(71) Applicant: HANGZHOU NANOCHAP ELECTRONICS CO., LTD., Hangzhou (CN)

(72) Inventors: Jiawei Yang, Hangzhou (CN); Nhan Tran, Hangzhou (CN); Xuyan Yang, Hangzhou (CN)

(73) Assignee: HANGZHOU NANOCHAP ELECTRONICS CO., LTD., Hangzhou (CN)

( * ) Notice: Subject to any disclaimer, the term of this patent is extended or adjusted under 35 U.S.C. 154(b) by 174 days.

(21) Appl. No.: 16/962,788

(22) PCT Filed: May 16, 2018

(86) PCT No.: PCT/CN2018/087067
§ 371 (c)(1),
(2) Date: Jul. 16, 2020

(87) PCT Pub. No.: WO2019/140817
PCT Pub. Date: Jul. 25, 2019

(65) Prior Publication Data
US 2020/0353268 A1 Nov. 12, 2020

(30) Foreign Application Priority Data
Jan. 17, 2018 (CN) .......................... 20181004418.8

(51) Int. Cl.
*A61N 1/05* (2006.01)
*A61N 1/375* (2006.01)
(Continued)

(52) U.S. Cl.
CPC ......... *A61N 1/3756* (2013.01); *A61N 1/0543* (2013.01); *A61N 1/3754* (2013.01);
(Continued)

(58) Field of Classification Search
CPC .. A61N 1/3756; A61N 1/0543; A61N 1/3754; B81B 7/007; B81B 2201/06;
(Continued)

(56) References Cited

U.S. PATENT DOCUMENTS

2007/0290308 A1* 12/2007 Kim .................... B81C 1/00301
257/414
2009/0321107 A1* 12/2009 Taylor ................. H01M 50/191
174/137 R
(Continued)

*Primary Examiner* — Ankit D Tejani
*Assistant Examiner* — Joshua Brendon Solomon
(74) *Attorney, Agent, or Firm* — Hauptman Ham, LLP

(57) ABSTRACT

The present invention relates to the field of medical devices, and specifically to a packaging structure and a packaging method for a retinal prosthesis implanted chip, including a high-density stimulation electrode component processed by a glass substrate, wherein the stimulation electrode component comprises the glass substrate, and a plurality of stimulation electrodes and a pad structure provided on the glass substrate; the stimulation electrodes are formed through cutting out metal pins on the metal and then pouring with glass; the stimulation electrode component is connected to an ASIC chip; a glass packaging cover is covered on the ASIC chip, the glass packaging cover is provided with a metal feedthrough structure for communicating with the stimulation chip; and the packaging cover covers and encapsulates the pad structure. In the packaging structure of the present invention, the substrate and the packaging cover are both made of a glass material, and thereby enable manufacture of a high-density stimulation electrode array, and the metal feedthrough structure is directly used on the glass (Continued)

cover, which facilitates wiring and achieves good sealing performance of the package cover.

6 Claims, 5 Drawing Sheets

(51) Int. Cl.
*B81B 7/00* (2006.01)
*B81C 1/00* (2006.01)

(52) U.S. Cl.
CPC .......... *B81B 7/007* (2013.01); *B81C 1/00301* (2013.01); *B81B 2201/06* (2013.01); *B81B 2207/012* (2013.01); *B81B 2207/095* (2013.01); *B81C 2203/0109* (2013.01); *B81C 2203/0792* (2013.01)

(58) Field of Classification Search
CPC ........ B81B 2201/012; B81B 2207/095; B81C 2203/0109; B81C 2203/0792
See application file for complete search history.

(56) References Cited

U.S. PATENT DOCUMENTS

| | | | | |
|---|---|---|---|---|
| 2011/0114840 A1* | 5/2011 | Yamazaki | ............... | H01L 23/26 29/841 |
| 2015/0371929 A1* | 12/2015 | Tai | ..................... | H01L 23/4985 623/6.63 |
| 2016/0030753 A1* | 2/2016 | Shah | ................... | A61N 1/3754 607/116 |

* cited by examiner

PACKAGING STRUCTURE AND PACKAGING METHOD FOR RETINAL PROSTHESIS IMPLANTED CHIP

RELATED APPLICATIONS

The present application is a National Phase of International Application Number PCT/CN2018/087067, filed May 16, 2018, and claims the priority of China Application No. 201810044188.8, filed Jan. 17, 2018.

TECHNICAL FIELD

The present invention relates to the field of medical devices, and specifically to a packaging structure and a packaging method for a retinal prosthesis implanted chip.

BACKGROUND

Implantable nerve stimulators have a wide range of applications in medicine, and micro-electrode stimulators, as an important tool for the treatment of neurological diseases, have received more and more attention from people and have become an important research direction at present.

Currently, most of the stimulation electrodes of retinal prostheses are flexible MEMS micro-electrodes. Such a micro-electrode is connected to the package body on the outer wall of an eyeball through multiple connecting wires, and a chip is not required to be connected to the stimulation electrodes inside the eyeball, so very strict airtight packaging is not necessary, and you only need to wrap silicone on the surface.

In order to improve the performance of retinal prostheses, some research directions are to increase the density of stimulation electrodes and improve the stimulation effect thereof. However, when the density of stimulation electrodes is increased, the number of stimulation electrodes becomes larger, and the number of connecting wires becomes very large, which results in inconvenient in connection and a large surgical trauma. In order to solve this problem, our research direction is to set an ASIC chip on the stimulation electrodes inside an eyeball.

For this kind of retinal stimulation electrodes that needs to be flip-chip connected to ASIC chip on the micro-electrodes, the chip must be hermetically packaged, on the one hand, to ensure that the chips would not be corroded by the body fluid environment of the human body, and on the other hand, to prevent the substances in the package body from causing adverse reactions on the tissues of the human body.

However, how to ensure the sealing effect and improve its sealing reliability is a very difficult problem.

SUMMARY

In order to improve the packaging reliability of the above chip, the present invention provides a packaging structure for a retinal prosthesis implanted chip, which is specifically described as follows.

A packaging structure for a retinal prosthesis implanted chip, comprising: a stimulation electrode component, wherein the stimulation electrode component comprises a glass substrate, wherein a plurality of stimulation electrodes and a pad structure for establishing signal connection with the outside provided on the glass substrate; an ASIC chip further connected onto the stimulation electrode component; and a packaging cover covering the ASIC chip, wherein the packaging cover is made of a glass, and further a metal feedthrough structure for establishing communication with the stimulation electrode component provided on the packaging cover, wherein the packaging cover encapsulates the pad structure and the ASIC chip. In the present invention, the substrate of the stimulation electrodes is a glass substrate, and the high density-stimulation electrodes can be formed by processing on the substrate made of a glass material. In order to ensure that the packaging cover performs tight packaging on the substrate made of a glass material, the packaging cover is also made of a glass material, and both the ASIC chip and the pad structure are packaged in the glass cover; and signal output is achieved directly through the connection between the metal feedthrough structure on the glass cover and the pad structure, so that there is no need to pull out a connecting wire from the inside of the package body. Therefore, the sealing effect is good.

Preferably, the stimulation electrode component has stimulation portions for stimulating the retina, the pad structure on the glass substrate is provided on the side opposite to the stimulation portions, and the metal feedthrough structure on the packaging cover is provided on the top of the packaging cover, penetrates the glass from top to bottom and is aligned with the pad structure. The pad structure is used for establishing signal connection with the outside. If the pad structure is connected onto the same side of the stimulation portions of the stimulation electrodes, it is apt to interfere with the stimulation portions during the packaging process. Thus, in the present invention, the pad structure on the glass substrate is provided on the side opposite to the stimulation portions.

Preferably, there are a plurality of pad structures and a plurality of metal feedthrough structures.

Preferably, the thermal expansion coefficient of the packaging cover matches the thermal expansion coefficient of the metal feedthrough structure therein.

Preferably, the glass cover and the glass substrate are sealed together by means of laser welding.

Preferably, a UBM layer is deposited on the a contact surface of the package cover and the glass substrate, a UBM layer is also deposited on a contact portions of the peripheral of the glass substrate and the glass cover, and a UBM layer is also deposited on a contact portion of the metal feedthrough structure and the pad structure, wherein the glass cover and the periphery of the glass substrate are connected by means of Au—Au bonding, and the metal feedthrough structure on the glass cover and the pad structure on the glass substrate are also connected by means of Au—Au bonding.

Preferably, the glass cover and the glass substrate are sealed together by means of laser welding, and the metal feedthrough structure on the glass cover and the pad structure on the glass substrate are connected by means of Au—Au bonding, tin welding, or laser welding.

Preferably, the pad structure and the metal feedthrough structure are connected through a signal connecting wire.

The present invention further provides a packaging method for a retinal prosthesis implanted chip, comprising the following steps:

S1: providing a metal underlayer and processing the metal underlayer to form a stimulation electrode component with a glass substrate, processing the stimulation electrode component to form a plurality of stimulation electrodes and a pad structure to realize the signal connection, and welding an ASIC chip onto the stimulation electrode component;

S2: forming a glass cover with a metal feedthrough structure by processing; and

S3: covering the glass substrate with the glass cover, aligning the metal feedthrough structure on the glass cover with the pad structure on the glass substrate and realizing the connection therebetween, and sealing the periphery of the glass cover and the glass substrate to realize the connection and packaging of the glass cover and the glass substrate.

Preferably, in the S1, the metal underlayer is processed by the following specific method:

(1): providing a metal underlayer, and cutting out a plurality of metal pins and the pad structure on the metal underlayer;

(2): filling the cut-out metal pins with glass, so that the cut-out metal pins are completely covered with glass;

(3) double-sided thinning of the metal underlayer after glass melt filling, wherein the glass covering layer on the cut side of the metal underlayer is thinned until the metal pins are exposed, and the metal underlayer on the other side of the metal underlayer is thinned and removed until a glass substrate surface formed by filling is completely exposed; and (4) processing one side of the product obtained by the above step so that the metal pins in the glass substrate protrude out of the glass surface to form stimulation portions, and the stimulation electrodes with the glass substrate are formed as a whole.

Preferably, in the S2, the glass material is processed to form the glass cover with a cavity, and then the metal feedthrough structure is embedded in the glass cover.

Preferably, in the S2, the method for processing the glass cover with the metal feedthrough is as follows:

(1): providing the metal underlayer, and cutting the metal underlayer to form the metal pins;

(2): filling the cut-out metal pins with glass; and (3): processing the metal underlayer filled with glass, thinning and removing the metal side, to form the glass structure with the metal feedthrough structure, and processing the glass structure to form the glass cover with an internal cavity.

Preferably, in the S3, the specific packaging process is as follows:

(1): depositing a UBM layer on the contact surface of the glass cover and the glass substrate, and depositing a UBM layer on the contact portion of the peripheral of the glass substrate and the glass cover;

(2): depositing a UBM layer on a contact portion of the feedthrough structure and the pad structure;

(3): placing the glass cover on the glass micro-substrate accurately, encapsulating the pad structure and the ASIC chip on the glass substrate in the glass cover, aligning the metal feedthrough structure on the glass cover with the pad structure on the glass substrate, and wherein the periphery of the glass cover is in close contact with the glass substrate; and (4): performing Au—Au thermocompression bonding on the position where the periphery of the glass cover and the glass substrate are in contact, and performing Au—Au thermocompression bonding on the position where the metal feedthrough structure on the glass cover and the pad structure are in contact.

Preferably, in the S3, the specific packaging process is as follows:

(1) placing the glass cover on the glass substrate, encapsulating the pad structure and the ASIC chip on the glass substrate in the glass cover, and aligning the metal feedthrough structure on the glass cover with the pad structure on the glass substrate; and realizing the connection between the metal feedthrough structure and the pad structure by means of Au—Au bonding, tin welding, or laser welding; and (2) making the periphery of the glass cover in close contact with the glass substrate, and performing laser welding on the position where the periphery of the glass cover contacts and the glass substrate.

Advantageous effects of the present invention:

1. the substrate of the stimulation electrodes and the packaging cover are both made of a glass material, and when the chip is packaged, the glass cover also encapsulates the pad structure on the glass substrate, to avoid the defect that the pad structure is exposed, and the problem of air tightness is easy to occur during welding;

2. a metal feedthrough structure is provided on the glass cover, and the metal feedthrough structure directly contacts with the pad structure on the glass substrate to realize the signal communication, which can conveniently achieve signal output and avoid problems of air tightness;

3. in the process of airtight packaging, the pad structure and the feedthrough structure on the glass cover are connected by means of Au—Au thermocompression bonding, the Au—Au thermocompression bonding method can realize the connection at a lower temperature, and avoid the impact of high temperatures on the chip; and 4. the stimulation electrode part is processed by glass filling, so that the high-density stimulation electrode component can be achieved.

Figure 1:
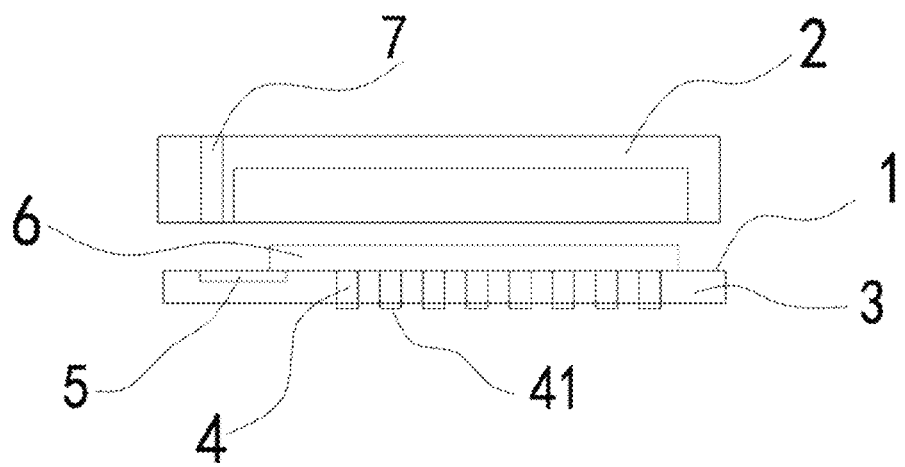
FIG. 1 is a schematic structural diagram of the stimulation electrode component in the present invention.
Figure 2:
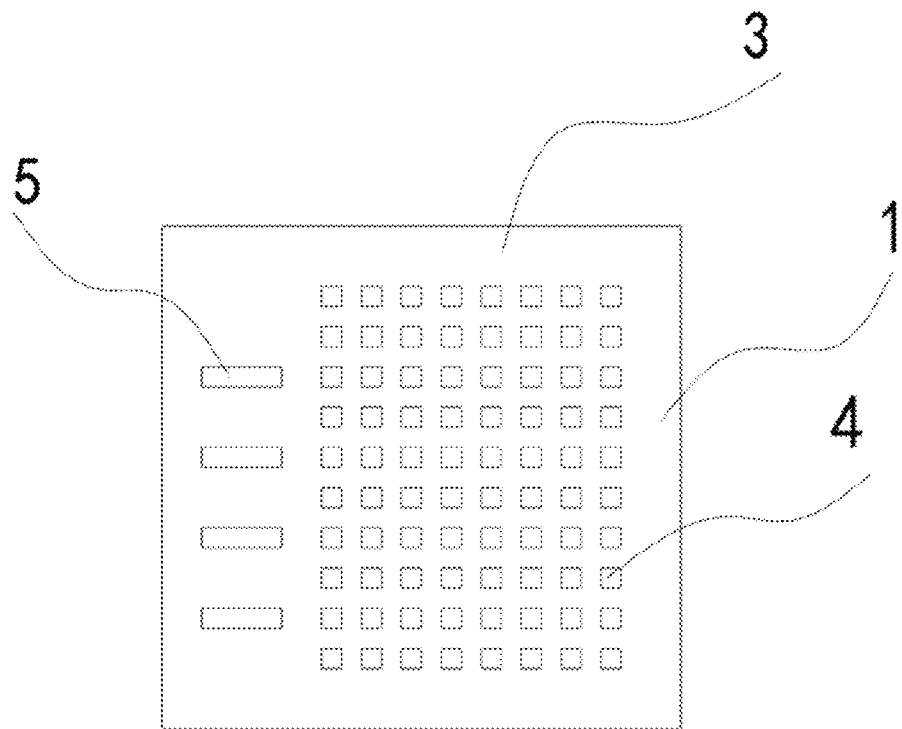
FIG. 2 is a schematic structural diagram of the glass substrate with metal pins formed by processing.
Figure 3:
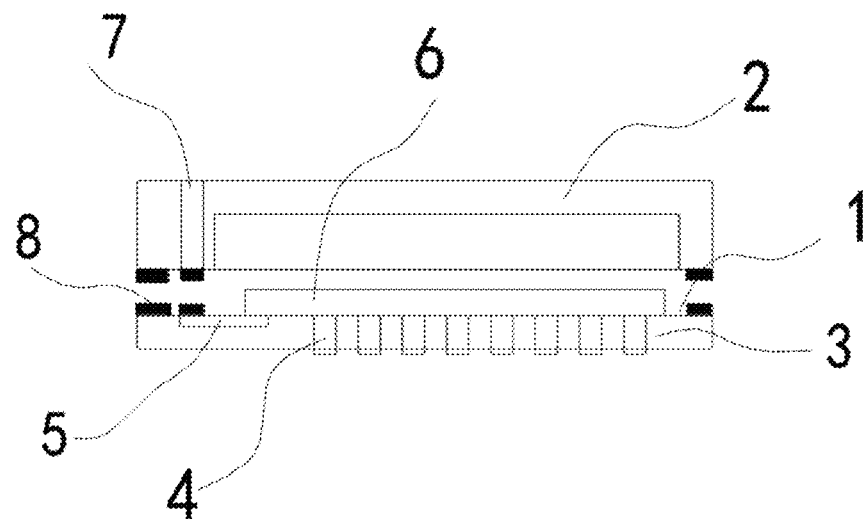
FIG. 3 is a schematic structural diagram of the package body according to Example 1 of the present invention.
Figure 4:
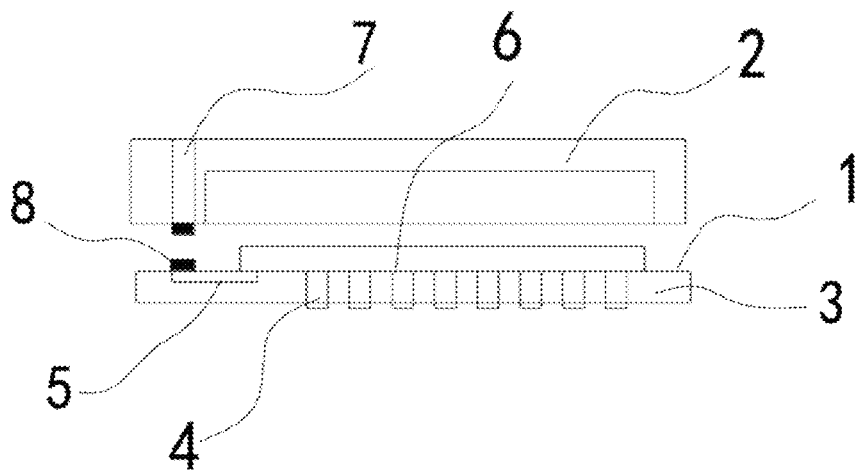
FIG. 4 is a schematic structural diagram of the package body according to Example 2 of the present invention.
Figure 5:
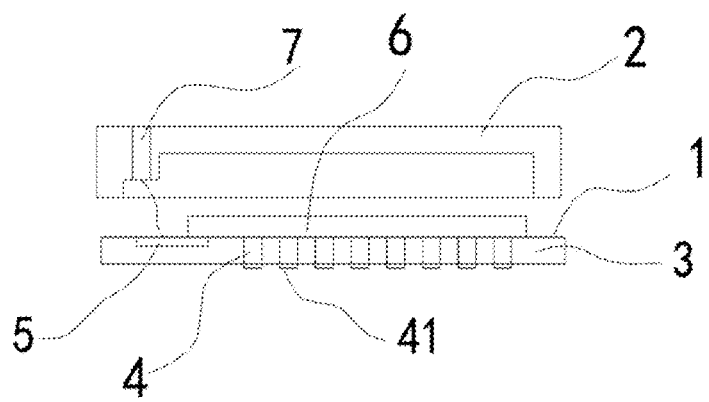
FIG. 5 is a schematic structural diagram of the package body according to Example 3 of the present invention.
Figure 6:
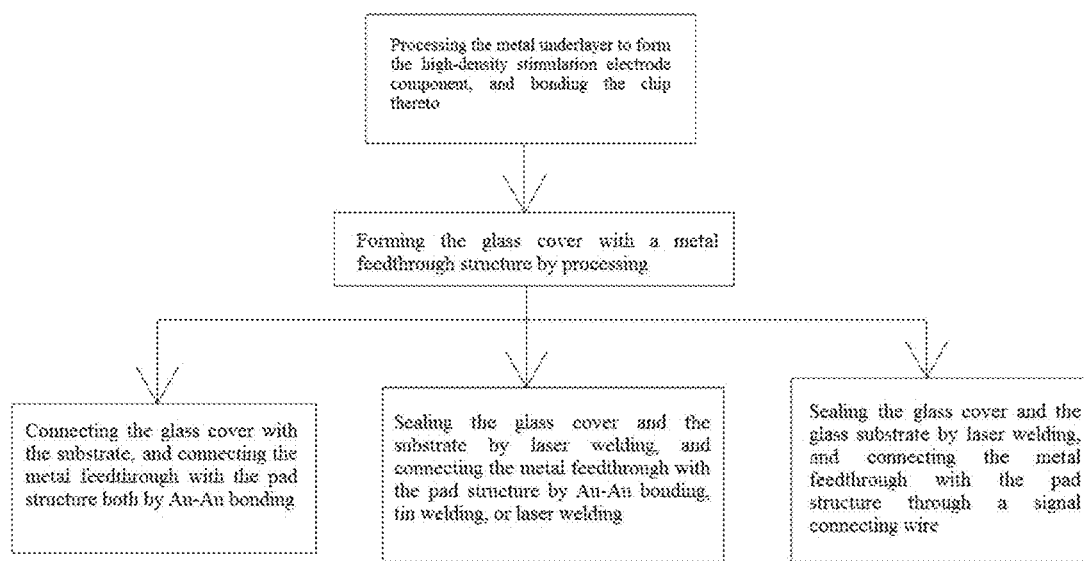
FIG. 6 is a schematic diagram of the packaging process in the present invention.
Figure 7:
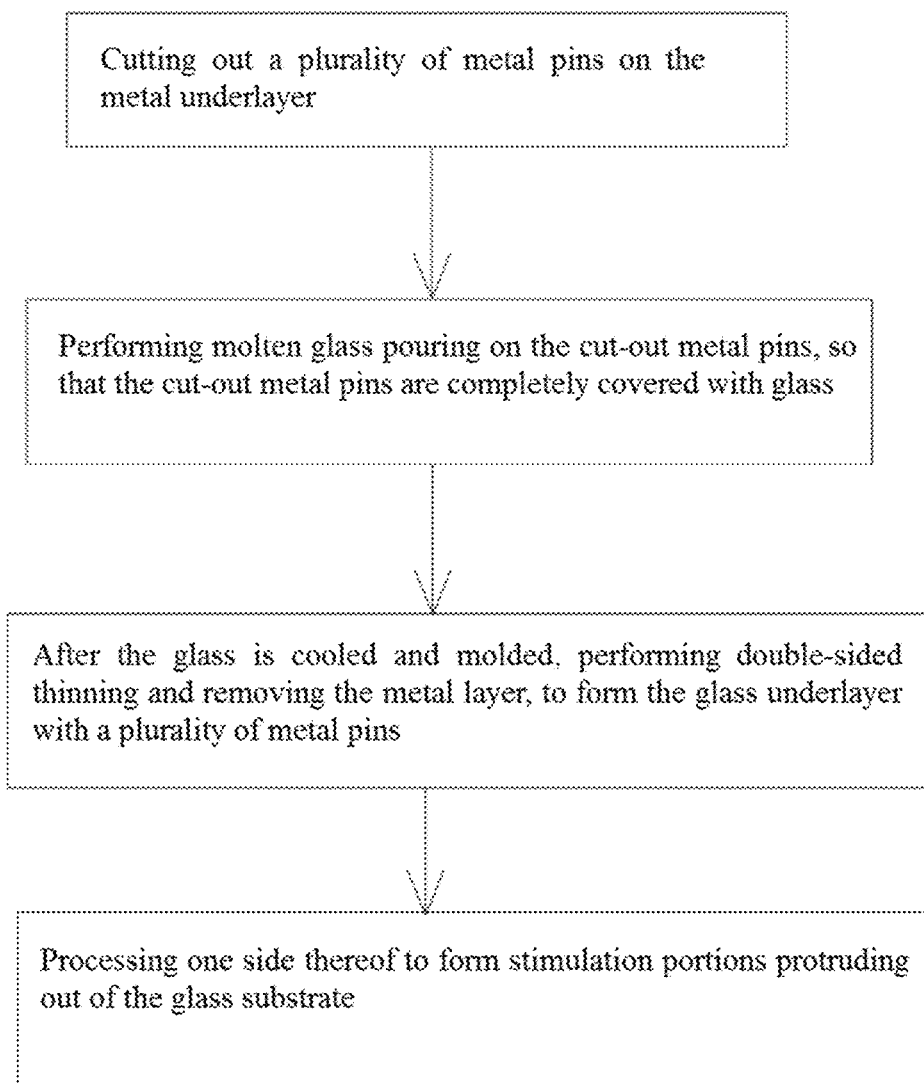
FIG. 7 is a schematic diagram of the process of processing a stimulation electrode with a glass substrate in the present invention.
Figure 8:
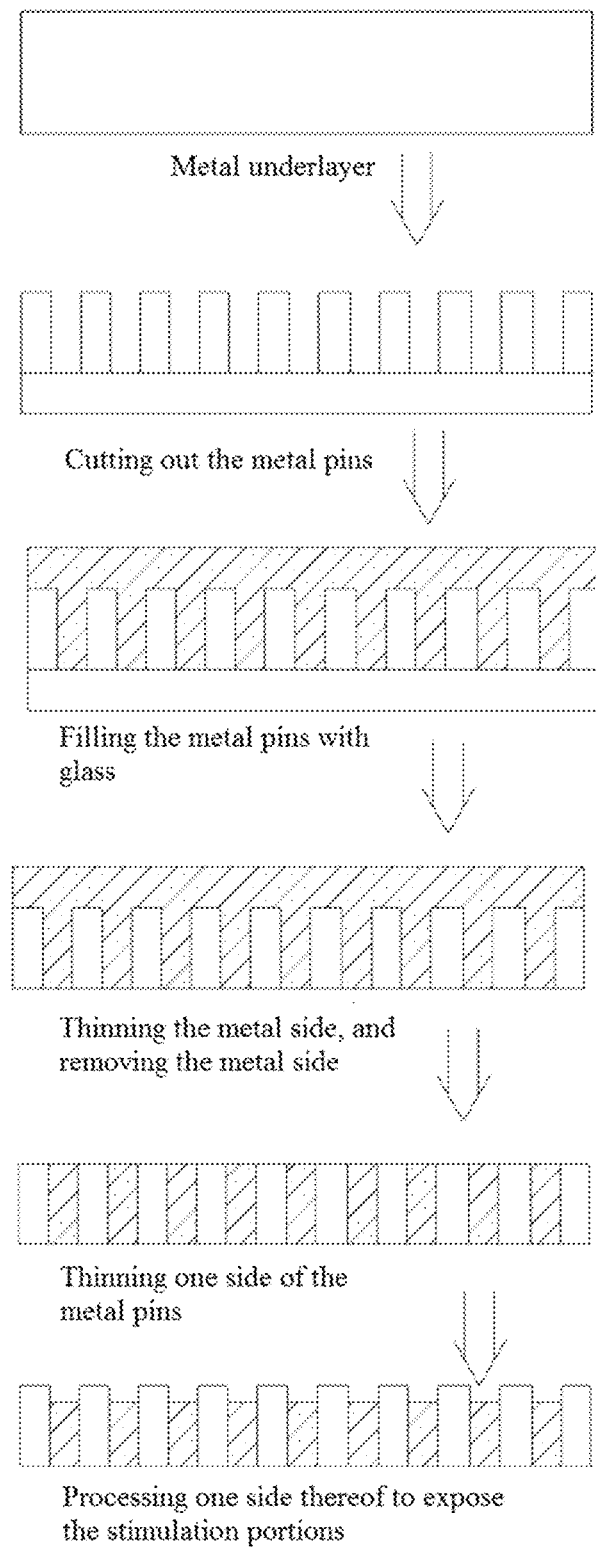
FIG. 8 is a schematic diagram of a stimulation electrode with a glass substrate processed in the present invention.

Wherein 1 is a stimulation electrode component, 2 is a packaging cover, 3 is a glass substrate, 4 is a stimulation electrode, 41 is a stimulation portion, 5 is a pad structure, 6 is an ASIC chip, 7 is a metal feedthrough structure, and 8 is a UBM deposition layer.

DETAILED DESCRIPTION

For the purposes of promoting an understanding of the present invention, the present invention will now be further described with reference to the attached drawings.

The present invention firstly shows a packaging structure for a retinal prosthesis implanted chip, comprising: a stimulation electrode component 1, which comprises a glass substrate 3, and a plurality of stimulation electrodes 4 and a pad structure 5 for realizing the signal connection with the outside provided on the glass substrate 3. The stimulation electrode component 1 is produced by pouring glass after cutting a metal underlayer, so that a high density of stimulation electrodes can be produced. An ASIC chip 6 is further connected onto the stimulation electrode component. The ASIC chip 6 is connected to the stimulation electrodes by flip-chip bonding. A small number of signal transmission main control points are arranged on the ASIC chip, and these number of signal transmission main control points are interconnected with the communication component outside the eyeball through a small number of connecting wires, so that the number of intermediate connecting wires is greatly reduced. Since the ASIC chip 6 is implanted to the inside of the eyeball of the human body, in order to prevent the body fluid from eroding the chip and causing damage, the ASIC chip 6 is covered with a packaging cover 2. The packaging cover 2 is further provided with a metal feedthrough structure 7 for realizing the signal communication with the stimulation electrode component 1. And the packaging cover 2 encapsulates the pad structure 5 and the ASIC chip 6. In order to ensure airtightness of the packaging, the packaging cover is also made of a glass material, and both the ASIC chip 6 and the pad structure 5 are encapsulated in the glass cover; and signal output is achieved directly through the connection between the metal feedthrough structure 7 and the pad structure 5 on the glass cover 2, so that there is no need to pull out a connecting wire from the inside of the package body. Therefore, the sealing effect is good.

The pad structure 5 on the glass substrate 3 is provided on the side opposite to the stimulation portions 41, and the metal feedthrough structure 7 on the packaging cover 2 is provided on the top of the packaging cover 2 to penetrate the glass from top to bottom and align with the pad structure 5. The pad structure 5 is used to achieve signal connection with the outside. If the pad structure 5 is connected to the same side of the stimulation portions 41 of the stimulation electrodes 4, this may cause the signal connecting wire to affect the bonding of the stimulation portions and the retina, and affect the stimulation effect. Thus, in the present invention, the pad structure on the glass substrate is provided on the side opposite to the stimulation portions.

In order to avoid a gap between the metal feedthrough structure and the glass packaging cover due to thermal expansion and contraction during welding or processing, generally, the thermal expansion coefficient of the glass packaging cover 2 matches the thermal expansion coefficient of the metal feedthrough structure 7 therein.

The glass substrate 3 is covered with the glass cover 2. In order to achieve the effective packaging of the glass cover on the glass substrate, the connection between the pad structure and the metal feedthrough structure and the sealing of the glass cover and the glass substrate can be achieved by means of Au—Au bonding, which is specifically carried out as follows:

A UBM layer is deposited on the contact surface of the inside of the package cover 2 and the glass substrate 3, a UBM layer is also deposited on the contact portion of the peripheral of the glass substrate and the glass cover, and a UBM layer is also deposited on a contact portion of the metal feedthrough structure and the pad structure, wherein the glass cover and the periphery of the glass substrate are connected by means of Au—Au bonding, and the metal feedthrough structure on the glass cover and the pad structure on the glass substrate are also connected by means of Au—Au bonding.

The glass cover 2 and the glass substrate 3 may alternatively be sealed together by laser welding, and the metal feedthrough structure 7 on the glass cover and the pad structure 5 on the glass substrate 3 are connected by means of Au—Au bonding, tin welding, or laser welding.

The present invention further provides a packaging method for a retinal prosthesis implanted chip, comprising the following steps:

S1: providing a metal underlayer and processing the metal underlayer to form a stimulation electrode component with a glass substrate, wherein the stimulation electrode component comprises a plurality of stimulation electrodes and a pad structure to realize the signal connection; and welding an ASIC chip onto the stimulation electrode component;

S2: forming a glass cover with a metal feedthrough structure by processing; and

S3: covering the glass substrate with the glass cover, aligning the metal feedthrough structure on the glass cover with the pad structure on the glass substrate and realizing the connection therebetween, and sealing the periphery of the glass cover and the glass substrate to realize the connection and packaging of the glass cover and the glass substrate.

In the above processing method, the metal underlayer is processed by the following specific method in S1:

(1): providing a metal underlayer, and cutting out a plurality of metal pins on the metal underlayer, wherein this cutting manner may be cutting by using laser or cutting by using machinery, the cut-out metal pins are arranged in an array, and generally a pad structure is also cut out during the cutting;

(2): performing molten glass pouring between the cut-out metal pins by pouring molten glass on the metal pins, so that the cut-out metal pins are completely covered with glass;

(3) after the glass pouring layer is cooled and molded, double-sided thinning of the metal underlayer after molten glass pouring, wherein the glass covering layer on the cut side of the metal underlayer is thinned until the metal pins are exposed, and the metal underlayer on the other side of the metal underlayer is thinned until a glass substrate surface formed by pouring is completely exposed, in which way, the metal layer can be completely removed, leaving a nerve stimulator with a glass substrate and a plurality of stimulation electrodes integrally formed thereon; and (4) after the above steps are completed, further processing one side of the product obtained by the above step, that is, removing the glass substrate around the metal pins on one side by means of cutting, so that the metal pins in the glass substrate protrude out of the glass surface form stimulation portions, and the stimulation electrodes with the glass substrate are formed as a whole.

Since the nerve stimulator needs to be implanted into human tissues, there are strict requirements for biocompatibility of the materials used in the nerve stimulator, and thus the metal underlayer processed to form the metal pins and the pad structure is generally made of a metal material with biocompatibility, such as titanium, platinum, iridium, tantalum, gold or an alloy thereof.

The thickness of the metal underlayer is generally between 0.3 mm and 1.5 mm, so that a proper length of the cut-out metal pin can be guaranteed, and meanwhile, the processing efficiency in the subsequent process of double-sided thinning would not be reduced because the metal layer is too thick. Furthermore, in order to guarantee a proper thickness of the glass substrate and a proper stimulation length of the stimulation portion, the depth of the cut-out metal pin is generally 150 µm to 1000 µm, the diameter or the side length of the cut-out metal pin is 50 µm to 150 µm, and the specific numerical values thereof may vary according to actual needs.

In the subsequent operation process, since the signal connection needs to be achieved on the nerve stimulator or the nerve stimulator needs to be bonded with a chip, the whole substrate is often heated, and in order to avoid a gap between the glass substrate and the metal pins therein due to temperature rise, the thermal expansion coefficient of the molten and poured glass matches the thermal expansion coefficient of the metal underlayer.

In the above processing method, the glass cover with a metal feedthrough structure is formed by the following processing method in the S2:

cutting a glass material to form a glass cover with a cavity, and then embedding a metal feedthrough structure in the glass cover.

Or the following method may be employed:

(1): providing a metal underlayer and cutting the metal underlayer to form metal pins;

(2): performing molten glass pouring on the cut-out metal pins; and (3): processing the metal underlayer that has been subjected to molten glass pouring by thinning and removing the metal side to form a glass structure with a metal feedthrough, and cutting the glass structure to form a glass cover with an internal cavity.

In the above processing method, the specific packaging method in the S3 is as follows.

Example 1

(1): depositing a UBM layer on the contact surface of the glass cover and the glass substrate, and also depositing a UBM layer on the contact portion of the peripheral surface of the glass substrate with the glass cover;

(2): depositing a UBM layer on the contact portion of the metal feedthrough structure and the pad structure;

(3): accurately placing the glass cover on the glass micro-substrate, encapsulating the pad structure and the ASIC chip on the glass substrate in the glass cover, and align the metal feedthrough structure on the glass cover with the pad structure on the glass substrate, and the periphery of the glass cover is in close contact with the glass substrate; and (4): performing Au—Au thermocompression bonding on the position where the periphery of the glass cover and the glass substrate are in contact, and performing Au—Au thermocompression bonding on the position where the metal feedthrough structure on the glass cover and the pad structure are in contact.

At this time, the metal feedthrough structure on the glass cover achieves is signal connected to the pad structure by means of Au—Au thermocompression bonding, and the periphery of the glass cover is also sealed to the metal substrate by Au—Au thermocompression bonding, wherein the thermocompression bonding temperature is generally between 150° C. and 400° C., so that the chip would not be damaged due to the excessive temperature.

Example 2

(1) placing the glass cover on the glass substrate, encapsulating both the pad structure and the ASIC chip on the glass substrate in the glass cover, and the metal feedthrough structure on the glass cover is aligned with the pad structure on the glass substrate; and achieving connection between the metal feedthrough structure and the pad structure by means of Au—Au bonding, tin welding, or laser welding; and (2) making the periphery of the glass cover and the glass substrate in close contact, and performing laser welding on the position where the periphery of the glass cover and the glass substrate are in contact.

At this time, the glass cover and the glass substrate are sealed together by laser welding, and the metal feedthrough structure on the glass cover and the pad structure on the glass substrate are connected by Au—Au bonding, tin-welding, laser welding or the like.

Example 3 sealing the glass cover and the glass substrate by laser welding or other welding means, and the metal feedthrough structure on the glass cover with the pad structure on the substrate are connected through a signal connecting wire.

The above Examples are merely preferred examples of the present invention and are not intended to limit the present invention. It should be noted that any modifications, equivalent substitutions, or improvements made without departing from the spirit and principles of the present invention shall be included in the protection scope of the present invention.

What is claimed is:

1. A packaging method for a retinal prosthesis implanted chip, comprising the following steps:
    S1: providing a metal underlayer and processing the metal underlayer to form a stimulation electrode component with a glass substrate, processing the stimulation electrode component to form a plurality of stimulation electrodes and a pad structure to realize the signal connection, and welding an ASIC chip onto the stimulation electrode component;
    S2: forming a glass cover with a metal feedthrough structure by processing; and
    S3: covering the glass substrate with the glass cover, aligning the feedthrough structure on the glass cover with the pad structure on the glass substrate and realizing the connection therebetween, and sealing the periphery of the glass cover and the glass substrate to realize the connection and packaging of the glass cover and the glass substrate.

2. The packaging method for the retinal prosthesis implanted chip according to claim 1, wherein in the S1, the metal underlayer is processed by the following specific method:
    (1): providing a metal underlayer, and cutting out a plurality of metal pins and the pad structure on the metal underlayer;
    (2): filling the cut-out metal pins with glass, so that the cut-out metal pins are completely covered with glass;
    (3) double-sided thinning of the metal underlayer after molten glass pouring, wherein the glass covering layer on the cut side of the metal underlayer is thinned until the metal pins are exposed, and the metal underlayer on the other side of the metal underlayer is thinned until a glass substrate surface formed by filling is completely exposed; and
    (4) processing one side of the product obtained by the above step so that the metal pins in the glass substrate form stimulation portions on the glass surface, and the stimulation electrodes with the glass substrate are formed as a whole.

3. The packaging method for the retinal prosthesis implanted chip according to claim 1, wherein in the S2, the glass material is processed to form the glass cover with a cavity, and then the metal feedthrough structure is embedded in the glass cover.

4. The packaging method for the retinal prosthesis implanted chip according to claim 1, wherein in the S2, the method for processing the glass cover with the metal feedthrough structure is as follows:

(1): providing the metal underlayer, and cutting the metal underlayer to form the metal pins;
(2): filling the cut-out metal pins with glass; and
(3): processing the metal underlayer filled with glass, thinning and removing the metal side, to form the glass structure with the metal feedthrough structure, and processing the glass structure to form the glass cover with the cavity.

5. The packaging method for the retinal prosthesis implanted chip according to claim 1, wherein in the S3, the specific process of connecting and encapsulating the glass cover and the glass substrate is as follows:
   (1): depositing a UBM layer on a contact surface of the glass cover and the glass substrate, and depositing a UBM layer on a contact portion of a peripheral of the glass substrate and the glass cover;
   (2): depositing a UBM layer on a contact portion of the metal feedthrough structure and the pad structure;
   (3): placing the glass cover on the glass substrate accurately, encapsulating the pad structure and the ASIC chip on the glass substrate, aligning the metal feedthrough structure on the glass cover with the pad structure on the glass substrate, and wherein the periphery of the glass cover is in close contact with the glass substrate; and
   (4): performing Au—Au thermocompression bonding on the position where the periphery of the glass cover and the glass substrate are in contact, and performing Au—Au thermocompression bonding on the position where the metal feedthrough structure on the glass cover and the pad structure are in contact.

6. The packaging method for the retinal prosthesis implanted chip according to claim 1, wherein in the S3, the specific packaging process is as follows:
   (1) placing the glass cover on the glass substrate, encapsulating the pad structure and the ASIC chip on the glass substrate in the glass cover, and aligning the metal feedthrough structure on the glass cover with the pad structure on the glass substrate; and realizing the connection between the metal feedthrough structure and the pad structure by means of Au—Au bonding, tin welding, or laser welding; and
   (2) making the periphery of the glass cover in close contact with the glass substrate, and performing laser welding on the position where the periphery of the glass cover contacts the glass substrate.

\* \* \* \* \*